(12) United States Patent
Blank et al.

(10) Patent No.: US 6,415,167 B1
(45) Date of Patent: Jul. 2, 2002

(54) FIBER OPTIC PROBE PLACEMENT GUIDE

(75) Inventors: Thomas B. Blank, Chandler; George Acosta, Phoenix; Mutua Mattu; Stephen L. Monfre, both of Gilbert, all of AZ (US)

(73) Assignee: Instrumentation Metrics, Inc., Chandler, AZ (US)

( * ) Notice: Subject to any disclaimer, the term of this patent is extended or adjusted under 35 U.S.C. 154(b) by 0 days.

(21) Appl. No.: 09/563,782

(22) Filed: May 2, 2000

(51) Int. Cl.[7] .............................................. A61B 5/00
(52) U.S. Cl. ..................... 600/344; 600/310; 600/322; 385/137
(58) Field of Search ........................ 600/344, 309–310, 600/322–324; 385/53–94, 137; 607/112; 356/39–42

(56) References Cited

U.S. PATENT DOCUMENTS

| | | | |
|---|---|---|---|
| 5,448,662 A | 9/1995 | Kittell et al. ................ 385/25 |
| 5,548,674 A | 8/1996 | Rondeau ..................... 385/72 |
| 5,636,634 A | 6/1997 | Kordis et al. |
| 5,655,530 A | 8/1997 | Messerschmidt |
| 5,661,843 A | 8/1997 | Rickenbach et al. ........ 385/147 |
| 5,671,317 A | * | 9/1997 | Weishaupt et al. .......... 385/137 |
| 5,956,150 A | | 9/1999 | Kanne ........................ 356/399 |
| 5,978,691 A | * | 11/1999 | Mills ........................... 600/344 |
| 6,014,756 A | * | 1/2000 | Raley ......................... 600/344 |
| 6,045,511 A | * | 4/2000 | Ott et al. .................... 600/504 |
| 6,152,876 A | * | 11/2000 | Robinson et al. .......... 600/322 |

\* cited by examiner

Primary Examiner—Eric F. Winakur
Assistant Examiner—Matthew Kremer
(74) Attorney, Agent, or Firm—Michael A. Glenn; Christopher Peil

(57) ABSTRACT

A fiber optic probe placement guide minimizes sampling errors during optical sampling of a tissue measurement site by allowing repeatable placement of the fiber optic probe at a targeted tissue measurement site. A mount, contoured to conform to the shape of the tissue measurement site, typically the arm of a human subject, contains an aperture for receiving a fiber optic probe. A temperature probe on the contact surface of the guide allows for monitoring of surface temperature within the vicinity of the tissue measurement site. Crosshair slots in the mount align with corresponding crosshairs at the tissue measurement site. The fiber optic probe placement guide is affixed to the tissue measurement site by means of adhesive tape or fastenable straps. Guideposts on the external surface of the mount are received by corresponding receptacles on a subject interface bearing the fiber optic probe to facilitate alignment of the fiber optic probe with the aperture.

42 Claims, 4 Drawing Sheets

FIBER OPTIC PROBE PLACEMENT GUIDE

BACKGROUND OF THE INVENTION

1. Field of the Invention

The invention relates to optical sampling of tissue in vivo. More particularly, the invention relates to a fiber optic probe placement guide and optical coupler for repeatably sampling a tissue measurement site in vivo.

2. Description of the Prior Art

Noninvasive prediction of blood analytes, such as blood glucose concentration, may employ NIR spectroscopic methods. A commonly assigned application, S. Malin and T. Ruchti, An Intelligent System For Noninvasive Blood Analyte Prediction, U.S. patent application Ser. No. 09/359,191; Jul. 22, 1999 describes a system for noninvasively predicting blood glucose concentrations in vivo, using NIR spectral analysis. Such NIR spectroscopy-based methods utilize calibrations that are developed using repeated in vivo optical samples of the same tissue volume. These successive measurements must yield a substantially repeatable spectrum in order to produce a usable calibration. The heterogeneous and dynamic nature of living human skin leads to sampling uncertainty in the in vivo measurement. Sampling differences can arise due to variable chemical composition and light scattering properties in tissue. As an example: because glucose is not uniformly distributed in tissue, a variation in the volume of tissue sampled is likely to lead to a variation in the strength of the glucose signal, even though glucose concentration in the tissue or blood remains constant. Variation in the placement and replacement of the fiber optic probe used for optical sampling at the measuring surface can lead to sampling in errors in two separate ways: variations in location of the probe can cause a different tissue volume to be sampled; varying the amount of pressure applied to the probe can alter the amount of tissue displaced, causing a larger or smaller tissue volume to be sampled. A change in optical sampling may lead to a variation in the spectral signal for a target analyte even though the concentration of the analyte in the blood or tissue remains unchanged. Furthermore, air gaps between the surface of the fiber optic probe and the surface of the tissue being sampled are another source of sampling error.

Various systems for guiding and coupling fiber optic probes are known. For example, M. Rondeau, High Precision Fiberoptic Alignment Spring Receptacle and Fiberoptic Probe, U.S. Pat. No. 5,548,674; Aug. 20, 1996 and R. Rickenbach and R. Boyer, Fiber Optic Probe, U.S. Pat. No. 5,661,843; Aug. 26, 1997 both disclose fiber optic probe guides utilizing ferrules through which a fiber optic cable or thread is longitudinally threaded. Both devices are connectors that couple fiber optic cables or threads to receptacles in various forms of medical equipment, or to other fiber optic cables. Neither device provides a means for repeatably coupling a fiber optic probe to a tissue measurement site.

T. Kordis, J. Jackson, and J. Lasersohn, Systems Using Guide Sheaths for Introducing, Deploying and Stabilizing Cardiac Mapping and Ablation Probes, U.S. Pat. No. 5,636,634; Jun. 10, 1997 describe a system that employs catheters and guide sheaths to guide cardiac mapping and ablation probes into the chambers of the heart during surgery or diagnostic procedures. The Kordis teachings are directed to surgical methods for the heart, and have nothing to do with optical sampling of tissue in vivo. Furthermore, the apparatus of Kordis, et al. would not be suitable for repeatably coupling a fiber optic probe to a tissue measurement site.

M. Kanne, Laser Mount Positioning Device and Method of Using the Same, U.S. Pat. No. 5,956,150; Sep. 21, 1999 describes a method for using an illumination device, such as a laser to align two components during an assembly process. The Kanne teachings are directed to a manufacturing process rather than optical sampling of tissue in vivo. The Kanne device does not provide any means for repeatably placing a probe guide at a tissue measurement site. It also has no way of monitoring the surface temperature at a tissue measurement site, or of minimizing surface temperature fluctuations and accumulation of moisture at a tissue measurement site.

D. Kittell, G. Hayes, and P. DeGroot, Apparatus for Coupling an Optical Fiber to a Structure at a Desired Angle, U.S. Pat. No. 5,448,662, Sep. 5, 1995 disclose an optical fiber support that is coupled to a frame for positioning an optical fiber at a desired angular position. As with the prior art previously described, the teachings of Kittell, et al. have nothing to do with optical sampling of tissue in vivo. Furthermore, the disclosed device allows an operator to immobilize an optical fiber so that it is maintained in a fixed position, but it does not offer a means of repeatably coupling a fiber optic probe to a tissue measurement site. It also has no way of monitoring the surface temperature at a tissue measurement site, or of minimizing accumulated moisture and temperature fluctuations at the site.

R. Messerschmidt, Method for Non-Invasive Blood Analyte Measurement with Improved Optical Interface, U.S. Pat. No. 5,655,530, Aug. 12, 1997 discloses an index-matching medium to improve the interface between a sensor probe and a skin surface during spectrographic analysis. Messerschmidt teaches a medium containing perfluorocarbons and chlorofluorocarbons. Since they are known carcinogens, chlorofurocarbons (CFC's) are unsuitable for use in preparations to be used on living tissue. Furthermore, use of CFC's poses a well-known environmental risk. Additionally, Messerschmidt's interface medium is formulated with substances that would be likely to leave artifacts in spectroscopic measurements.

It would be desirable to provide a placement guide for a fiber optic probe that coupled the probe to a tissue measurement site for in vivo optical sampling of the tissue. It would also be desirable to provide a means of assuring that the same tissue sample volume may be repeatably sampled, thus eliminating sampling errors due to probe placement. It would also be desirable to provide a way to minimize temperature fluctuations and disperse accumulated moisture at the tissue measurement site, thus eliminating further sources of sampling error. Additionally, it would be advantageous to provide a means of monitoring surface temperature at the tissue measurement site, therefore assuring that the temperature remains constant across repeated optical samples. Finally, it would be highly advantageous to provide an optical coupling fluid to provide a constant interface between a fiber optic probe and the skin at a tissue measurement site that is non-toxic and non-irritating and that doesn't introduce error into spectroscopic measurements.

SUMMARY OF THE INVENTION

The invention provides a fiber optic probe placement guide designed to provide repeatable sub-millimeter location accuracy on the skin surface of a tissue measurement site and a repeatable degree of tissue displacement. The major structural component of the fiber optic probe placement guide is a mount having a probe aperture, into which the fiber optic probe is inserted during use. The contact surface of the mount is curved to approximate the contour of the tissue measurement site, typically a site on a limb of a living subject. The mount incorporates structural features to minimize direct contact between the skin around the tissue measurement site and the contact surface in order to reduce temperature fluctuation and moisture accumulation at the site and on the probe, and to reproduce a small amount of tissue displacement in the vicinity of the tissue measurement site. The fiber optic probe placement guide has crosshair slots that are aligned with crosshairs at the tissue measurement site during repeated placements of the fiber optic probe placement guide in order to minimize optical sampling errors due to placement error. Guideposts on the exterior surface of the fiber optic probe placement guide fit into corresponding guidepost recesses on a subject interface bearing the fiber optic probe to facilitate alignment of the probe with the probe aperture.

During use, the fiber optic probe placement guide is fastened to the tissue measurement site using adhesive or straps. A subject interface bearing a fiber optic probe is directed toward the site; the guideposts are received by the guidepost recesses in the housing of the interface, and the probe is received by the probe aperture. An optical coupling fluid placed on the skin surface at the tissue measurement site eliminates sampling errors due to air gaps between the skin surface and the fiber optic probe.

The fiber optic probe placement guide is also equipped with a temperature probe so that skin temperature in the area directly adjacent the tissue measurement site may be monitored.

DETAILED DESCRIPTION

In spectroscopic analysis of living tissue, it is often necessary to optically sample the same tissue volume repeatedly, using a fiber optic probe. Sampling errors can be introduced into these measurements because of the difficulty of repeatedly placing the fiber optic probe at the precise location used in preceding measurements, and repeatably producing the same amount of tissue displacement. With each small variation in the location of the probe, or the amount of pressure placed on the probe, a slightly different tissue volume is sampled, introducing sampling errors into the measurements. The invention provides a fiber optic probe placement guide to achieve the goal of highly repeatable fiber optic probe placement at a targeted tissue measurement site.

Figure 1:
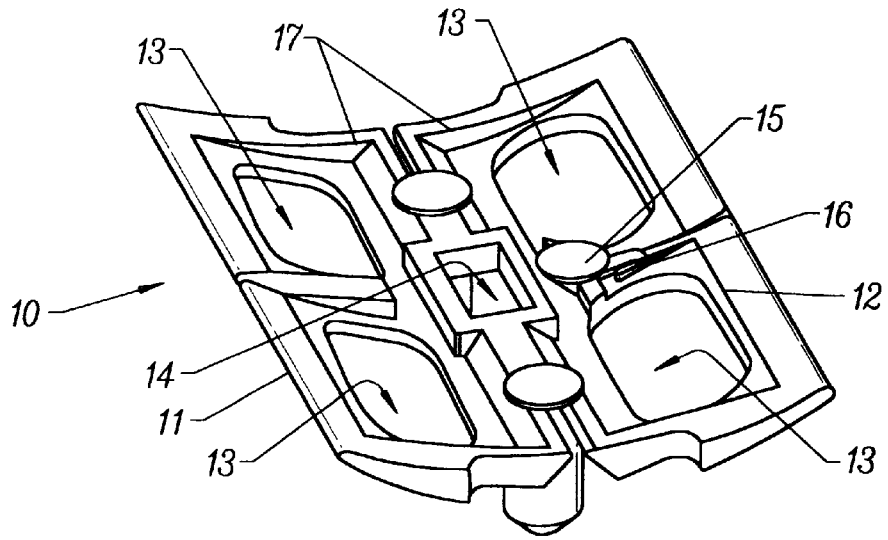
FIG. 1 provides a view of the contact surface of a fiber optic probe placement guide, according to the invention.

Referring now to FIG. 1, the fiber optic probe placement guide 10 with its contact surface 12 facing is shown. The major structural component of the fiber optic probe placement guide is a curved mount 11. As shown, the contour of the contact surface 12 approximates the contour of a body part at a tissue measurement site, typically a limb of a living subject. While some contact between the concave contact surface 12 of the mount 11 and the tissue measurement site is unavoidable during use, structural features of the mount minimize direct contact between the contact surface 12 and the tissue measurement site. It is desirable to minimize contact between the skin in the vicinity of the tissue measurement site and the contact surface for two reasons:

The structural and chemical properties of the underlying tissue layers are affected by the surface temperature and the relative humidity at the tissue measurement site. Therefore, maintaining the tissue measurement site at a constant surface temperature and preventing accumulation of moisture reduces sampling errors.

Minimized contact decreases the amount of tissue displacement from pressure on the tissue from the mount, therefore minimizing sampling errors due to variations in tissue displacement;

The mount 11 is highly skeletonized by providing cutaway openings 13. The surface area in direct contact with the tissue measurement site is further reduced by providing relieved areas 17 along the contact surface 12.

The mount includes a probe aperture 14 for receiving a fiber optic probe. The probe aperture 14 is centered vertically and horizontally and penetrates the body of the mount 11 from the exterior surface 20 to the contact surface 12. In the embodiment of FIG. 1, the probe aperture is rectangular to receive a rectangular fiber optic probe. However, the probe aperture may also be circular, hexagonal or triangular to receive probes of corresponding shape. The shape of the aperture should mimic the shape of the fiber optic probe it is to be used with, allowing them to fit together in a conventional male-female configuration. In order to monitor skin temperature within the vicinity of the tissue measurement site, a temperature probe 15, such as a thermistor, is provided. The temperature probe should be in direct and intimate contact with the surface of the tissue measurement site in order to provide accurate temperature readings. Therefore, a temperature probe mount 16 is provided that protrudes from the relieved contact surface 12 of the mount 11. In this manner, it is possible to maintain contact between the temperature probe and the tissue measurement site while still minimizing direct contact between the tissue measurement site and the contact surface 12 of the fiber optic probe placement guide. Furthermore, the temperature probe 15 is preferably located no more than 2mm from the edge of the probe aperture 14 in order to provide accurate temperature readings from within the immediate vicinity of the tissue measurement site.

Figure 2:
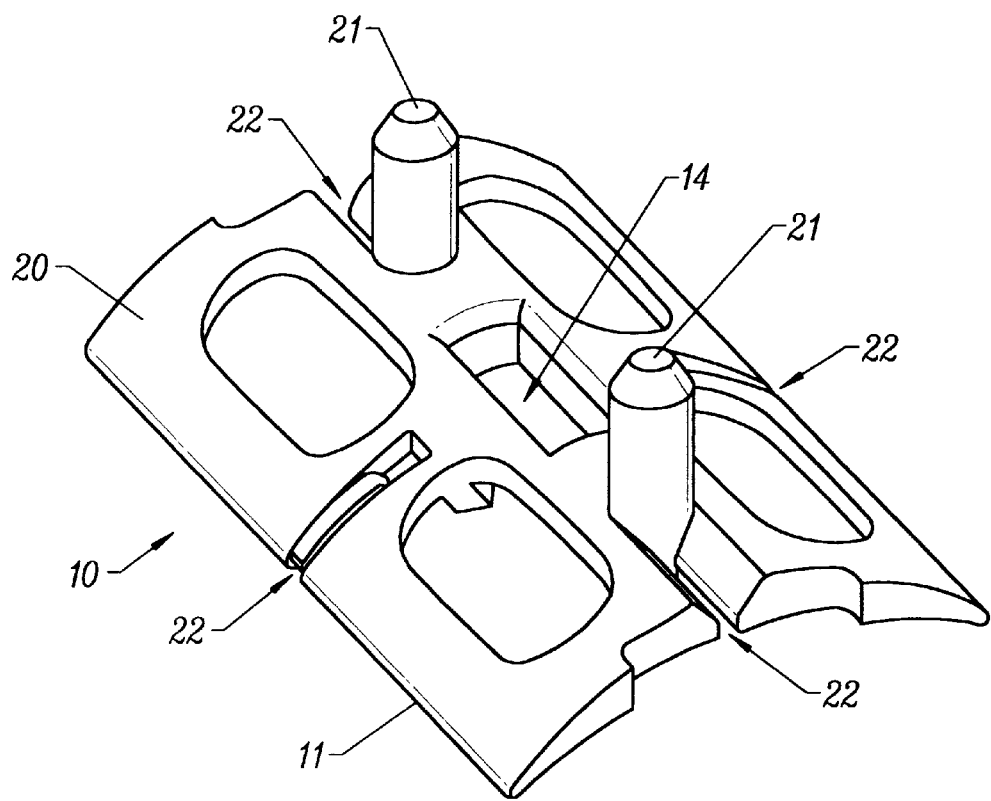
FIG. 2 provides a view of the exterior surface of the fiber optic probe placement guide of FIG. 1, according to the invention.

FIG. 2 provides a view of the exterior surface of the fiber optic probe placement guide 10. In the current embodiment, the exterior surface 20 is convex to correspond to the concave contact surface 12. The exterior surface is equipped with two outwardly protruding guideposts 21 having substantially cylindrical bodies and conical terminations. The two guideposts are situated opposing each other such that each guidepost is positioned approximately midway between one end of the mount 11 and one end of the probe aperture 14. Crosshair slots 22 are located at the midpoint of each of the four sides of the mount 11.

Figure 3:
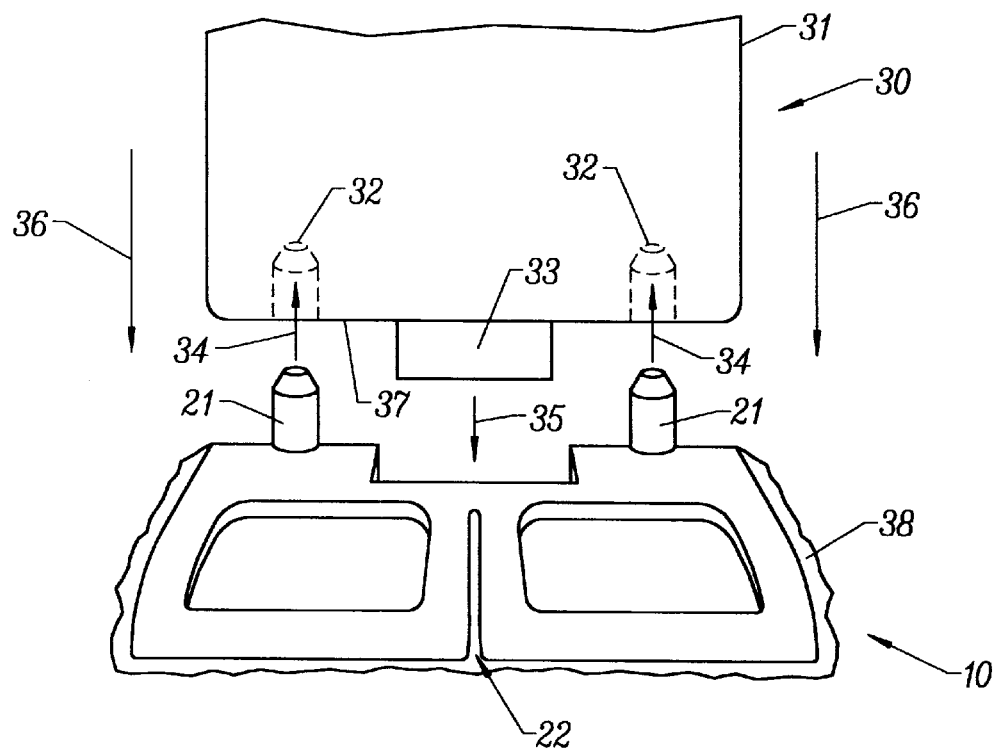
FIG. 3 illustrates the fiber optic probe placement guide of FIG. 1, in use. at a tissue measurement site, and a subject interface, according to the invention.

FIG. 3 shows the fiber optic probe placement guide in use. The fiber optic probe placement guide 10 is placed over a tissue measurement site. Tissue measurement is generally performed on a limb of a living subject. However, other regions of the body provide suitable sites as well. Additionally, the invention would find application in optical sampling of excised tissue specimens or tissue measurement sites on cadavers. An adhesive layer 38 may be used to fix the position of the fiber optic probe placement guide. The adhesive layer may take the form of a double-sided pressure-sensitive adhesive pad placed between the skin and the probe placement guide, or in the case of a disposable version of the probe placement guide, the adhesive layer may be applied directly to the contact surface of the probe placement guide. The adhesive layer is the preferred means of fastening the probe placement guide because it minimizes tissue displacement caused by downward pressure on the skin by the probe placement guide. Alternatively, adhesive tape, or one or more straps having releasable fasteners may be used to secure the invention.

Using the crosshair slots 22 as a template, crosshairs are drawn on the subject's skin using a marking pen or some other suitable tool. Subsequently, the location of the fiber optic probe placement guide may be repeated with sub-millimeter accuracy by aligning the crosshair slots 22 with the crosshairs drawn on the subject's skin. A subject interface unit 30 includes a housing 31 bearing a fiber optic probe 33. The fiber optic probe 33 protrudes from the interface side 37 of the housing 31 in a manner that allows it to be received by the probe aperture 14, as indicated by arrow 35. The housing 31 is also equipped with cylindrical guidepost recesses 32, represented in dashed lines. An operator lowers the subject interface unit 30 toward the tissue measurement site, shown by the arrows 36. As the interface unit 31 approaches the fiber optic probe placement guide, the guideposts 21 are received by the guidepost recesses 32, as indicated by the arrows 34, thus greatly facilitating the alignment of the probe 33 with the probe aperture 14. After the probe is fully seated in the probe aperture, the guideposts provide a stable placement, thus minimizing possible sampling errors due to movement of the interface unit 30 during optical sampling, and also preventing damage to the probe 33 due to inadvertently rotating it within the probe aperture 14 during use. The guideposts also serve to limit downward motion of the interface unit, thereby preventing the operator from placing excessive downward pressure on the unit and introducing sampling error due to inconsistent tissue displacement.

An important additional function of the fiber optic probe is to correct tissue displacement by the probe placement guide. Before the fiber optic probe is seated within the probe aperture, the skin at the tissue measurement site bulges upward into the fiber optic probe aperture as a result of tissue displacement by the probe placement guide. During use, the gentle downward pressure by the fiber optic probe helps to correct the upward bulge of the skin, significantly reducing another source of sampling error from variations in tissue displacement. In order to achieve this correction, the termination of the fiber optic probe should be flush with the contact surface at the tissue measurement site when the fiber optic probe is fully seated.

Figure 7:
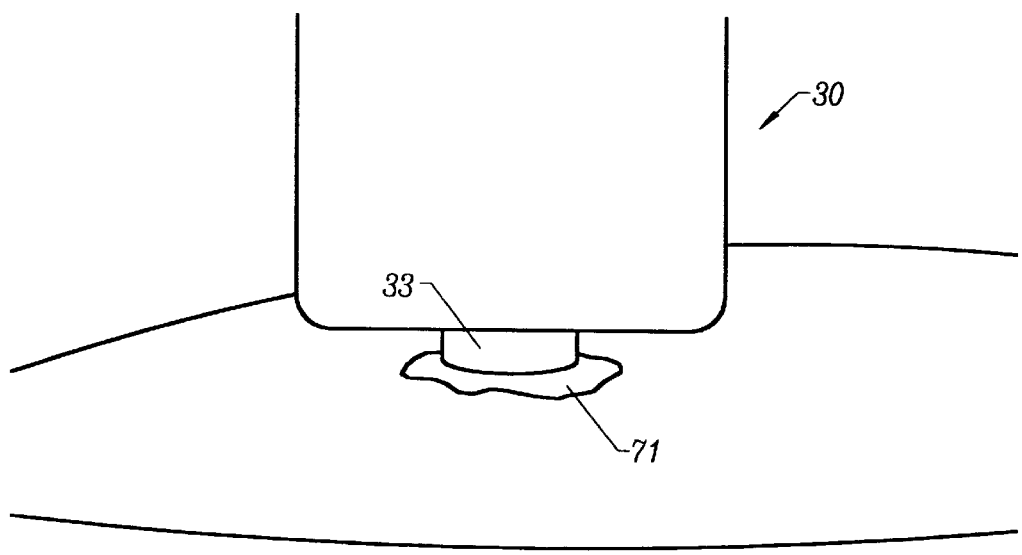
FIG. 7 shows a fiber optic probe and a tissue measurement site optically coupled by a layer of an optical coupling fluid.

The interface between the fiber optic probe and the skin surface at the tissue measurement site can also be a significant source of sampling error. Since the underlying tissue is not homogenous, the surface skin at the tissue measurement site may be uneven, with frequent irregularities. Coupling the relatively smooth surface of the fiber optic probe with the irregular skin surface leads to air gaps between the two surfaces. The air gaps create an interface between the two surfaces that adversely affects the measurement during optical sampling of tissue. As shown in FIG. 7, an amount of optical coupling fluid 71 between the fiber optic probe 33 and the skin of the tissue measurement site eliminates such gaps.

In a preferred embodiment, the optical coupling fluid is a perfluoro compound such as those known as FC-40 and FC-70, manufactured by 3M Corporation. Such compounds are inactive in the Near IR region, rendering them particularly well suited for optical sampling procedures employing Near IR spectra. Additionally, they have the advantage of being non-toxic and non-irritating, thus they can come into direct contact with living tissue, even for extended periods of time, without posing a significant health risk to living subjects. Furthermore, perfluoro compounds of this type are hydrophobic and are poor solvents; therefore they are unlikely to absorb water or other contaminants that will adversely affect the result during optical sampling. It is preferable that the optical sampling fluid be formulated without the addition of other substances such as alcohols or detergents, which may introduce artifacts into the optical sample. Finally, the exceptional stability of perfluoro compounds eliminates the environmental hazard commonly associated with chlorofluorocarbons.

Other fluid compositions containing perfluorocarbons and chlorofluorocarbons are suitable as optical coupling fluids: for example a blend of 90% polymeric chlorotrifluroethylene and 10% other fluorocarbons would have the desired optical characteristics. Chlorotrifluorethene could also be used. While these compositions have the desired optical characteristics, their toxicity profiles and their solvent characteristics render them less desirable than the previously described perfluoro compounds.

During use, a quantity of optical sampling fluid is placed at the interface of the tissue measurement site and the fiber optic probe so that the tissue measurement site and the fiber optic probe may be tightly optically coupled without leaving any air spaces between the two surfaces. In practice, one convenient way of placing the quantity of the optical sampling fluid at the interface between the tissue measurement site and the probe is to place a small amount of the fluid on the skin surface prior to placing the fiber optic probe, although it is easier to place it on the fiber-optic probe.

Figure 4:
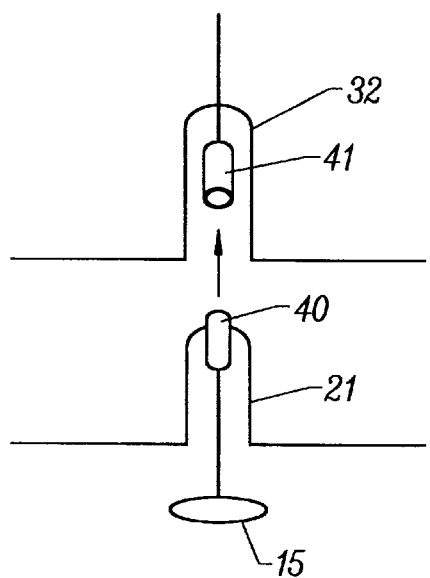
FIG. 4 illustrates an electrical connection between a temperature probe in the fiber optic probe placement guide of FIG. 1 and a subject interface unit, according to the invention.

During use, the temperature probe 15 is electrically connected with the interface unit 30 by means of pin-and-socket electrical contacts. As FIG. 4 shows, the temperature probe 15 is connected to a pin electrical contact 40 embedded in the guidepost 21. During use, the pin contact is received by a socket electrical contact 41 in the guidepost recess 32, thus establishing an electrical connection between the temperature probe and the interface unit 30. In this manner, electrical signals from the temperature probe are passed to processing components within the interface unit that convert the electrical signal into a temperature reading.

The current embodiment of the invention is preferably manufactured from a thermoplastic polymeric material such as ABS or polytetrafluoroethylene (PTFE) using a conventional injection molding process.

Figure 5:
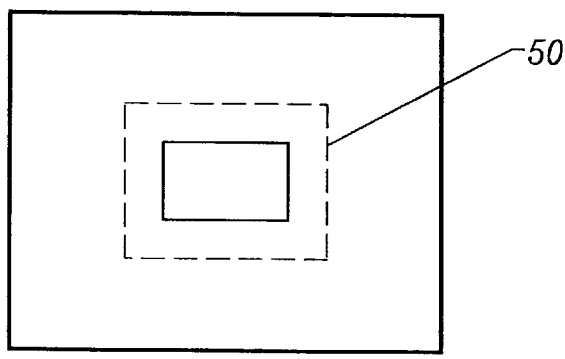
FIG. 5 shows an alternate embodiment of a fiber optic probe placement guide, fabricated from a flexible layer and incorporating a reinforcing insert surrounding the probe aperture, according to the invention.
Figure 6A:
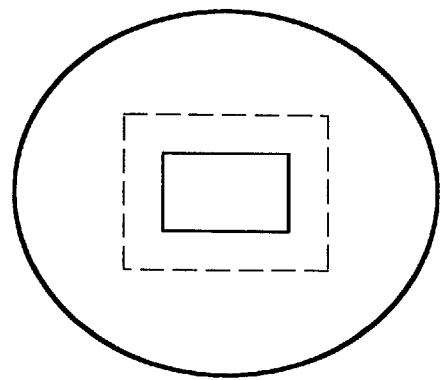
FIGS. 6A–6C show a variety of alternate shapes for the fiber optic probe placement guide of FIG. 5, according to the invention.
Figure 6B:
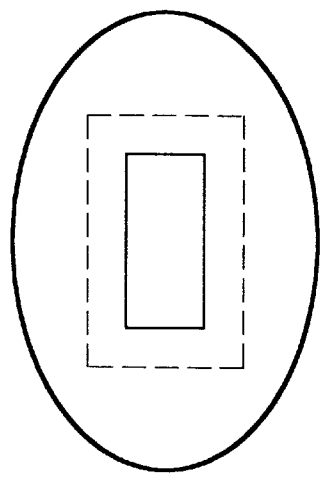
Figure 6C:
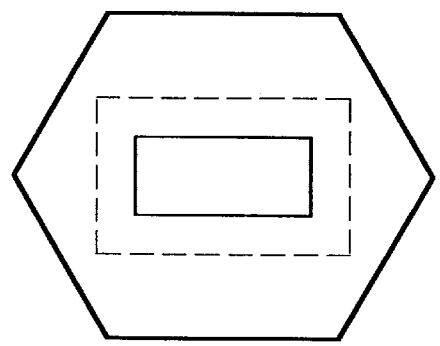

Other advantageous embodiments of the invention are possible. For example, the previously described embodiment is manufactured from a non-porous polymeric material, rendering it suitable for shorter periods of use, where the possible impact on the temperature and humidity at the tissue measurement site is not of great concern. An alternate embodiment, particularly well suited for longer periods of use, employs a layer fabricated from a flexible, breathable material such as GORE-TEX, manufactured by W. L. Gore and Associates, as the mount. As shown in FIG. 5, the layer incorporates a reinforced insert 50 around the probe aperture to lend the aperture the requisite structural stability. As shown in FIGS. 6A–6C, the mount may assume a circular, or oval or polygonal shape.

While previously described embodiments of the invention employ structural features to control temperature and humidity at the tissue measurement site passively, an alternative embodiment incorporates an airflow device, such as a small blower, to evaporate moisture from the fiber optic probe, the contact surface, and the tissue measurement site.

Further alternative embodiments of the invention employ three and four guideposts, respectively, along with corresponding guidepost recesses.

While the invented fiber optic probe placement guide allows highly repeatable probe placement at a targeted tissue measurement site, the invention may also be used to produce small sampling variations in a controlled manner by shifting the placement of the fiber optic probe in known increments across successive optical samples.

The invented fiber optic probe placement guide has been herein described in relation to optical sampling of tissue. One skilled in the art will appreciate that the invention may be applied in other settings requiring repeatable placement of a fiber optic probe.

The invention provides a means of limiting sampling errors during in vivo spectroscopic examination of tissue samples by providing highly repeatable fiber optic probe placement at a targeted tissue measurement site. Structural features of the invention minimize temperature fluctuations and accumulation of excess humidity at the tissue measurement site and on the fiber optic probe, and variations in tissue displacement, all sources of sampling error. A temperature probe in direct contact with the skin surface at the tissue measurement site allows the monitoring of skin temperature across successive measurements. An optical coupling fluid eliminates air spaces at the interface of the skin surface of the tissue measurement site and the fiber optic probe.

Although the invention is described herein with reference to certain preferred embodiments, one skilled in the art will readily appreciate that other applications may be substituted for those set forth herein without departing from the spirit and scope of the present invention. Accordingly, the invention should only be limited by the claims included below.

What is claimed is:

1. A fiber optic probe placement guide for repeatably coupling a fiber optic probe to a targeted measurement site, comprising:
    a mount, said mount having an exterior surface, a contact surface, and an outer edge, at least a portion of said contact surface being in contact with a surface at said measurement site during use;
    an aperture, defined by said mount, for receiving said fiber optic probe;
    a plurality of crosshair slots located at regular intervals about said outer edge; and
    a temperature probe mounted on said contact surface.

2. The fiber optic probe placement guide of claim 1, further comprising one or more guideposts protruding from said exterior surface, wherein said guideposts are aligned with and received by corresponding guide post recesses in a subject interface during use, wherein said fiber optic probe is born by said subject interface.

3. The fiber optic probe placement guide of claim 1, wherein said measurement site comprises a tissue measurement site and said measurement site surface comprises skin at said tissue measurement site.

4. The fiber optic probe placement guide of claim 3, wherein said contact surface is contoured such that its shape approximates the surface contour at said tissue measurement site.

5. The fiber optic probe placement guide of claim 2, wherein said temperature probe is mounted no more than 2mm from an edge of said aperture, and wherein said temperature probe is in direct contact with said surface at said measurement site.

6. The fiber optic probe placement guide of claim 5, wherein said temperature probe is electrically connected to a pin electrical contact in one of said guideposts, and wherein said pin contact is in direct contact with a socket electrical contact located within one of said guidepost recesses during use.

7. The fiber optic probe placement guide of claim 1, wherein said mount is relieved and skeletonized, so that contact of said measurement site with a surrounding environment is maximized and contact between said measurement site and said mount is minimized.

8. The fiber optic probe placement guide of claim 2, wherein said mount has opposing ends, and wherein said guideposts comprise a pair of guideposts, each one of said pair of guideposts being situated close to one of said opposing ends of said mount.

9. The fiber optic probe placement guide of claim 8, wherein said aperture is horizontally and vertically centered between said pair of guideposts.

10. The fiber optic probe placement guide of claim 8, wherein said aperture is rectangular in shape.

11. The fiber optic probe placement guide of claim 8, wherein said aperture is any of circular, triangular, and hexagonal in shape.

12. The fiber optic probe placement guide of claim 1, wherein said mount is substantially rectangular.

13. The fiber optic probe placement guide of claim 12, wherein said plurality of crosshair slots comprises four crosshair slots, each of said crosshair slots located at a midpoint of a side of said mount, and wherein said crosshair slots align with corresponding crosshairs at said measurement site during use.

14. The fiber optic probe placement guide of claim 1, wherein said mount is any of circular, oval and polygonal in shape.

15. The fiber optic probe placement guide of claim 1, further comprising means for removably attaching said fiber optic probe placement guide over said measurement site, so that said fiber optic probe placement guide is held in a fixed position.

16. The fiber optic probe placement guide of claim 15, wherein said attachment means comprises any of:
    an adhesive layer between said contact surface and said measurement site; and
    adhesive tape.

17. The fiber optic probe placement guide of claim 15, wherein said attachment means comprises one or more straps.

18. The fiber optic probe placement guide of claim 1, wherein said fiber optic probe placement guide is manufactured from a thermoplastic polymer material.

19. The fiber optic probe placement guide of claim 1, wherein said fiber optic probe placement guide is manufactured from a breathable membrane material.

20. The fiber optic probe placement guide of claim 19, wherein said mount further comprises a reinforced insert surrounding said aperture.

21. An apparatus for optically sampling a tissue measurement site repeatably, comprising:

a subject interface, said subject interface comprising:
a housing
a fiber optic probe contained within said housing;
said housing having an interface side and defining one or more recesses in said interface side, each of said one or more recesses having therein a socket electrical contact; and
a fiber optic probe placement guide for repeatably coupling said fiber optic probe to said tissue measurement site, comprising:
a mount, said mount having an exterior surface, a contact surface, and an outer edge, at least a portion of said contact surface being in contact with a skin surface at said tissue measurement site during use;
an aperture, defined by said mount, for receiving said fiber optic probe;
a plurality of crosshair slots disposed at regular intervals about said outer edge; and
a temperature probe mounted on said contact surface; and
an optical coupling fluid, wherein a quantity of said optical coupling fluid is placed at an interface of said tissue measurement site and said fiber optic probe, so that said skin surface and said fiber optic probe are tightly optically coupled.

22. The apparatus of claim 21, wherein said contact surface is contoured such that its shape approximates the surface contour at said tissue measurement site.

23. The apparatus of claim 21, further comprising:
at least one guidepost protruding from said exterior surface, wherein said at least one guidepost is adapted to be aligned with and received by said recess in a subject interface incorporating said fiber optic probe.

24. The apparatus of claim 23, wherein said temperature probe is mounted no more than 2mm from an edge of said aperture, and wherein said temperature probe is in direct contact with said skin surface.

25. The apparatus of claim 24, wherein said temperature probe is electrically connected to a pin electrical contact in one of said guideposts, and wherein said pin contact is in direct contact with a socket electrical located within one of said interface recesses during use.

26. The apparatus of claim 22, wherein said mount is relieved and skeletonized, so that contact of said measurement site with a surrounding environment is maximized and contact between said measurement site and said mount is minimized.

27. The apparatus of claim 23, wherein said mount has opposing ends, and wherein said guideposts comprise a pair of guideposts, each one of said pair of guideposts being situated close to one of said opposing ends.

28. The apparatus of claim 27, wherein said aperture is horizontally and vertically centered between said pair of guideposts.

29. The apparatus of claim 28, wherein said aperture is rectangular in shape.

30. The apparatus of claim 21, wherein said mount is substantially rectangular.

31. The apparatus of claim 30, wherein said plurality of crosshair slots comprises four crosshair slots, each of said crosshair slots located at a midpoint of a side of said mount, and wherein said crosshair slots align with corresponding crosshairs at said tissue measurement site during use.

32. The apparatus of claim 21, further comprising:
means for removably attaching said fiber optic probe placement guide over said measurement site, so that said fiber optic probe placement guide is held in a fixed position during use.

33. The apparatus of claim 32, wherein said attachment means comprises any of:
an adhesive layer placed between said contact surface and said measurement site; and
adhesive tape.

34. The apparatus of claim 32, wherein said attachment means comprises one or more straps.

35. The apparatus of claim 21, wherein said fiber optic probe placement guide is manufactured from a thermoplastic polymer material.

36. The apparatus of claim 21, wherein said fiber optic probe placement guide is manufactured from a breathable membrane material.

37. The apparatus of claim 21, wherein said optical coupling fluid comprises one or more perfluoro compounds.

38. The apparatus of claim 37, wherein said optical coupling fluid consists of one or more perfluoro compounds.

39. The apparatus of claim 37, wherein said optical coupling fluid consists essentially of one or more perfluoro compounds.

40. An optical coupling fluid consisting essentially of:
one or more perfluoro compounds, wherein a quantity of said optical coupling fluid is placed at an interface of an optical probe and a measurement site, so that said probe and said measurement site are tightly optically coupled.

41. The optical coupling fluid of claim 40, wherein said measurement site is a tissue measurement site.

42. The optical coupling fluid of claim 40, wherein said optical coupling fluid consists of one or more perfluoro compounds.

* * * * *